United States Patent
Douglas et al.

(10) Patent No.: US 6,582,573 B2
(45) Date of Patent: *Jun. 24, 2003

(54) MEMBRANE BASED ELECTROCHEMICAL TEST DEVICE

(75) Inventors: Joel S. Douglas, Los Altos Hills, CA (US); Jeffrey N. Roe, San Ramon, CA (US); John H. Priest, Everett, WA (US); David A. Hasker, San Jose, CA (US)

(73) Assignee: Amira Medical, Scotts Valley, CA (US)

( * ) Notice: Subject to any disclaimer, the term of this patent is extended or adjusted under 35 U.S.C. 154(b) by 19 days.

This patent is subject to a terminal disclaimer.

(21) Appl. No.: 09/878,774

(22) Filed: Jun. 8, 2001

(65) Prior Publication Data

US 2002/0020632 A1 Feb. 21, 2002

Related U.S. Application Data

(63) Continuation of application No. 09/401,062, filed on Sep. 22, 1999, now Pat. No. 6,245,215, which is a continuation of application No. 09/164,405, filed on Sep. 30, 1998, now Pat. No. 6,001,239.
(60) Provisional application No. 60/060,488, filed on Sep. 30, 1997.

(51) Int. Cl.[7] ............................................. G01N 27/327
(52) U.S. Cl. ............................... 204/403.1; 204/403.11
(58) Field of Search ...................... 204/403.14, 403.1, 204/403.11, 403.09

(56) References Cited

U.S. PATENT DOCUMENTS

| | | | |
|---|---|---|---|
| 3,271,591 A | 9/1966 | Orshinsky | 327/500 |
| 3,983,076 A | 9/1976 | Rockstad et al. | 252/519.4 |
| 4,178,415 A | 12/1979 | Ovshinsky et al. | 428/446 |
| 4,226,898 A | 10/1980 | Ovshinsky et al. | 438/483 |
| 4,938,860 A | 7/1990 | Wogoman | 204/403.05 |
| 4,963,814 A | 10/1990 | Parks et al. | 323/274 |

(List continued on next page.)

FOREIGN PATENT DOCUMENTS

| | | |
|---|---|---|
| DE | 43 00 499 | 7/1994 |
| EP | 0 255 291 | 7/1985 |
| EP | 0 351 892 A2 | 5/1988 |
| EP | 0351 891 A | 1/1990 |
| EP | 0470 290 A | 2/1992 |
| EP | 0592 805 A | 4/1994 |
| EP | 0710 835 A | 5/1996 |

OTHER PUBLICATIONS

Yokohama, Kenji, et al., "Amperometric Glucose Sensor Using Silicon Oxide Deposited Gold Electrodes", pp. 469–475, Research Center for Advanced Science and Technology, University of Tokyo (Tokyo, Japan), Oct. 30, 1990, Doc. No. XP 0020411662.

Cobbold, Richard S.C., *Transducers for Biomedical Measurements: Principles and Applications*, p. 343–349, John Wiley & Sons (New York). 1974.

Japan Patent Office, "Patents Abstracts of Japan", Pub. No. 60095343, May 28, 1985.

*Primary Examiner*—Nam Nguyen
*Assistant Examiner*—Alex Noguerola
(74) *Attorney, Agent, or Firm*—Woodward, Emhardt, Moriarty, McNett & Henry LLP

(57) ABSTRACT

An electrochemical test device is provided for determining the presence or concentration of an analyte in an aqueous fluid sample. The electrochemical test device includes a working electrode and a counter electrode made of an amorphous semiconductor material. The working electrode is overlaid with a reagent capable of reacting with an analyte to produce a measurable change in potential which can be correlated to the concentration of the analyte in the fluid sample. The test device optionally contains a reference electrode made of an amorphous semiconductor material having a reference material on the reference electrode.

4 Claims, 3 Drawing Sheets

U.S. PATENT DOCUMENTS

| | | |
|---|---|---|
| 4,999,582 A | 3/1991 | Parks et al. .................. 324/438 |
| 4,999,632 A | 3/1991 | Parks ......................... 341/167 |
| 5,001,048 A | 3/1991 | Taylor et al. .................. 435/4 |
| 5,243,516 A | 9/1993 | White ....................... 435/287.2 |
| 5,312,590 A * | 5/1994 | Gunasingham ........... 204/403.1 |
| 5,391,250 A | 2/1995 | Cheney, II et al. ......... 156/268 |
| 5,413,690 A * | 5/1995 | Kost et al. ................ 205/777.5 |
| 5,437,999 A | 8/1995 | Diebold et al. ........ 204/403.11 |
| 5,804,048 A | 9/1998 | Wong et al. ........... 204/403.09 |
| 6,001,239 A | 12/1999 | Douglas et al. ............. 205/778 |
| 6,245,215 B1 * | 6/2001 | Douglas et al. ............. 205/775 |

* cited by examiner

MEMBRANE BASED ELECTROCHEMICAL TEST DEVICE

This application is a continuation of application Ser. No. 09/401,062, filed on Sep. 22, 1999 which is now U.S. Pat. No. 6,245,215 B1 which is a continuation of application Ser. No. 09/164,405, filed Sep. 30, 1998 which is now U.S. Pat. No. 6,001,239 which claims the benefit of provisional application Ser. No. 60/060,488 filed Sep. 30, 1997.

BACKGROUND OF THE INVENTION

1. Field of the Invention

The present invention relates to an electrochemical test device suitable for determining the presence or concentration of chemical and biochemical components (analytes) in aqueous fluid samples and body fluids such as whole blood or interstitial fluid. Additionally, this invention relates to a method of using such test devices for determining the presence or concentration of an analyte and to processes for preparing such a test devices.

2. State of the Art

Medical studies have demonstrated that the incidence of serious complications resulting from diabetes, such as vision loss and kidney malfunction, can be significantly reduced by careful control of blood glucose levels. As a result, millions of diabetics use glucose testing devices daily to monitor their blood glucose concentrations. Additionally, a wide variety of other blood testing devices are used to determine the presence or concentration of other analytes, such as alcohol or cholesterol, in aqueous samples, such as blood.

Such blood testing devices typically employ either a dry chemistry reagent system or an electrochemical method to test for the analyte in the fluid sample. In recent years, electrochemical testing systems have become increasingly popular due to their small size and ease of use. Such electrochemical testing systems typically use electrochemistry to create an electrical signal which correlates to the concentration of the analyte in the aqueous sample.

Numerous electrochemical testing systems and related methods are known in the art. For example, European Patent Publication No. 0 255 291 B1, to Birch et al., describes methods and an apparatus for making electrochemical measurements, in particular but not exclusively for the purpose of carrying out microchemical testing on small liquid samples of biological, e.g. of clinical, origin.

European Patent Publication No. 0 351 891 B1, to Hill et al., teaches a method of making an electrochemical sensor by printing. The sensor is used to detect, measure or monitor a given dissolved substrate in a mixture of dissolved substrates, most specifically glucose in body fluid.

U.S. Pat. No. 5,391,250, to Cheney II et al., teaches a method of fabricating thin film electrochemical sensors for use in measuring subcutaneous or transdermal glucose. Fabrication of the sensors comprises placing a thin film base layer of insulating material onto a rigid substrate. Conductor elements for the sensors are formed on the base layer using contact mask photolithography and a thin film cover layer.

U.S. Pat. No. 5,437,999, to Diebold et al., teaches a method of fabricating thin film electrochemical devices which are suitable for biological applications using photolithography to define the electrode areas. The disclosures of each of the above patent specifications are incorporated herein by reference in their entirety.

An excellent reference on materials and process for fabricating electronic components is Charles A. Harper, Handbook of Materials and Processes for Electronics, 1984, Library of Congress card number 76-95803. It provides detail process information on thick film, thin film and photo resist processes.

Existing electrochemical testing systems, however, have certain limitations from the perspective of the end user or the manufacturer. For example, some electrochemical testing systems are difficult or costly to manufacture. As a result, such devices are too expensive to be used on a daily basis by, for example, diabetics. Other electrochemical testing systems are not sufficiently accurate to detect certain analytes at very low concentrations or to give reliable measurements of the analyte's concentration. Additionally, many electrochemical devices are too large to be easily carried by those needing to test their blood on a regular basis throughout the day. Thus, a need exists for improved electrochemical test devices.

SUMMARY OF THE INVENTION

The present invention utilizes amorphous semiconductor applied with thin film manufacturing techniques and membranes which have a skin on each planar surface to provide an electrochemical test device suitable for determining the presence or concentration of analytes in aqueous fluid samples. By using amorphous semiconductor materials applied with film manufacturing techniques and dual skin membranes, uniform electrochemical test devices having well-defined reproducible electrode areas can be manufactured economically.

In particular, the test devices of this invention have very uniform surface areas which reduce the variability of the electrochemical test. In this regard, it has been found that the surface area of the electrodes and the accuracy of applying the reagent are critical to producing an accurate test. If the surface area is not consistent from test to test then each of the test devices must be individually calibrated to insure accurate readings. The test devices of the present invention permit highly accurate electrochemical analyte measurements to be performed on very small aqueous fluid samples without the need for individual calibration of each test device. The present inventions provide for the accurate reproduction of the test devices by using controlled deposition methods, such as sputtering or vapor deposition and smooth skin membranes to form the electrodes with consistent size and surface morphology from device to device in continuous production. These devices can also be readily manufactured due to the lower cost and the flexible nature of the amorphous semiconductor materials which facilitates production by continuous roll processing versus the step and repeat printing methods currently employed. The ability to use continuous processing to fabricate the device, such as continuous processes utilizing continuous roll coating, continuous roll sputtering, continuous systems utilizing contact masks, results in high volume manufacturing capability and substantial cost reductions over the step and repeat processes. Additionally, the amorphous nature of the conductors electrodes and constructed and used according to this invention eliminates problems found in prior test devices which utilize conventional conductor and semiconductor materials, which are crystalline in nature or are noble metals and, as a result, require flat and rigid substrates to prevent cracking during manufacture, distribution or use. The membrane in the present invention is the earlier for the indicating reagent and forms the surface for the electrode formation. The membrane comprises the matrix in which the reagent is carried or impregnated and comprises the two exterior skin surfaces on which the electrodes are placed. The skin surfaces can be smooth skin suitable for carrying the electrodes and can be porous to pass the aqueous fluid samples or can have pores sized to screen or block selected components from aqueous fluid sample, such as red blood cells in a blood sample.

Dry electrochemical test devices fall into two primary configurations. The first configuration utilizes two electrodes, i.e., a working electrode and a counter electrode. The second configuration utilizes three electrodes, i.e., a working electrode, a counter electrode and a reference electrode. The use of the reference electrode and a reference material provides a fixed reference for the test. The test devices of the present invention are well suited for a two electrode system however, a contact mask could be employed during sputtering to create a surface with two electrodes.

Accordingly, in one of its aspects, the present invention provides an electrochemical test device for determining the presence or concentration of an analyte in an aqueous fluid sample, said electrochemical test device comprising:

(a) a nonconductive surface;

(b) a working electrode comprising an amorphous semiconductor material affixed to the non-conductive surface of a double skin membrane, said working electrode having an first electrode area, a first lead and a first contact pad;

(c) a counter electrode comprising an amorphous semiconductor material affixed to the opposite nonconductive surface of a double skin membrane, said counter electrode having an second electrode area, a second lead and a second contact pad; and (d) a reagent capable of reacting with the analyte to produce a measurable change in potential which can be correlated to the concentration of the analyte in the fluid sample, said reagent being imbibed into the membrane matrix between the two electrode surfaces.

In another embodiment of this invention, the test device further comprises a reference electrode comprising an amorphous semiconductor material affixed to the non-conductive surface, said reference electrode having an electrode area, a lead, and a contact pad, and wherein at least a portion of the electrode area is overlaid with a reference material. Preferably, the reference material is a silver/silver chloride layer, a mercury/mercury chloride layer or a platinum/hydrogen material. This electrode could be either the counter electrode or an independent third electrode.

In a preferred embodiment of this invention, the test device further comprises a blood separating membrane with two skin surfaces. The blood separating membrane separates whole blood samples into highly colored and relatively clear fluid portions before analysis. The blood separating membrane effectively blocks or filters red blood cells and allows essentially clear fluid to pass to the test reagent imbibed in the membrane matrix. As a result, the analyte is measured in the clear fluid portion of the sample contacting the electrodes thereby substantially eliminating the red blood cells from the reaction and minimizing interference from the cells present in blood. This embodiment has the additional benefit of keeping the test site from drying out and thereby improves the performance of test devices designed for small sample sizes, such as in the 1 to 5 microliter range.

Preferably, the membrane is selected from polysulphone, polyethersulphone, or nylon and is cased with a tight pore skin on each side and a relatively isotropic matrix between each skin surface The skin pore size is relatively tight approximately 0.1 to 0.5 microns in size and the isotropic matrix being 0.5 microns or greater in pore size. The tight pore size provides a uniform surface morphology on which the amorphous semiconductor electrodes are formed according to this invention. Better surface morphology of the membrane results in a more consistent surface for the amorphous semiconductor electrodes. This provides improved accuracy of test results and consistency of performance.

Preferably, the amorphous semiconductor material used in this invention is amorphous silicon oxide. More preferably, the amorphous silicon oxide is doped with lithium, potassium, or a similar conducting ion to increased conductivity. Doping with lithium is particularly preferred. However, amorphous carbon, gold, silver or other conductor materials which do not interfere with the electrochemistry of the reagent system are also suitable. The amorphous semiconductor material can be applied by using various techniques including sputtering, evaporation, vapor phase deposition or other thin film deposition technique to form a conductive layer on the membrane surface The surface texture of the amorphous semiconductor material is preferably less than 13 micro inches or 0.33 microns. However, rougher textures can be used depending on the accuracy of the desired test device.

The reagent employed in the electrochemical test device is typically selected based on the analyte to be tested and the desired detection limits. The reagent preferably comprises an enzyme and a redox mediator. When the analyte to be detected or measured is glucose, the enzyme is preferably glucose oxidase and the redox mediator is potassium ferrocyanide.

The electrochemical test device of the present invention is used to determine the presence or concentration of an analyte in an aqueous fluid sample. Accordingly, in one of its method aspects, the present invention provides a method for determining the presence or concentration of an analyte in an aqueous fluid sample, said method comprising:

(a) providing an electrochemical test device comprising: (i) double skinned membrane; (ii) a working electrode comprising an amorphous semiconductor material affixed to the membrane surface, said working electrode having an first electrode area, a first lead and a first contact pad area; (iii) a counter electrode comprising an amorphous semiconductor material affixed to the non-conductive surface, said counter electrode having a second electrode area, a second lead, and a second contact pad; and (iv) a reagent capable of reacting with the analyte to produce a measurable change in potential which can be correlated to the concentration of the analyte in the fluid sample, said reagent being imbibed into the membrane matrix between the two electrode surfaces;

(b) inserting the electrochemical test device into a meter device;

(c) applying a sample of an aqueous fluid to the membrane area of the working electrode;

(d) reading the meter device to determine the presence or concentration of the analyte in the fluid sample.

In another embodiment, the test device employed in this method further comprises a reference electrode comprising an amorphous semiconductor material affixed to the counter electrode membrane surface, said reference electrode having a third electrode area, a third lead, and a third contact pad, and wherein at least a portion of the third electrode area is overlaid with a reference material.

Preferably, the reference material is a silver/silver chloride layer, a mercury/mercury chloride layer or a platinum/hydrogen material. Silver/silver chloride is a particularly preferred reference material. The separation of the counter electrode conductive path and reference electrode is accomplished by using a mask to create the different geometries on the same surface.

Preferably, the membrane is selected from polysulphone, polyethersulphone, or nylon and is cased with a tight pore skin on each side and a relatively isotropic matrix between each skin surface The skin pore size is relatively tight approximately 0.1 to 0.5 microns in size and the isotropic matrix being 0.5 microns or greater in pore size. The tight pore size provides a uniform surface morphology on which the amorphous semiconductor electrodes are formed according to this invention. Better surface morphology of the membrane results in a more consistent surface for the amorphous semiconductor electrodes. This provides improved accuracy of test results and consistency of performance.

As discussed above, the present invention utilizes amorphous semiconductor materials and thin manufacturing techniques to provide electrochemical test devices. Thin film technologies can be used to create the amorphous semiconductor material conductive layers and electrodes according to this invention. Accordingly, in one of its process aspects, the present invention provides a process for preparing an electrochemical test device suitable for determining the presence or concentration of an analyte in an aqueous fluid sample, said process comprising the steps of:

(a) providing a skinned membrane having a first and an opposite second surface;

(b) depositing an amorphous semiconductor material on said first surface to form a conductive layer, (c) depositing an amorphous semiconductor material on said opposite second surface to form a conductive layer (d) applying a reagent to the membrane which is imbibed into the membrane matrix between the two surfaces, said reagent being capable of reacting with an analyte in an aqueous fluid sample to produce a measurable change in potential which can be correlated to the concentration of the analyte in the fluid sample.

In another embodiment, step (c) of this process further comprises forming a reference electrode comprising a third electrode having a third electrode area, a third lead and a third contact pad. This is accomplished by using a mask to form the two distinct electrodes and in a step (e) forming a silver chloride surface.

In a preferred embodiment, step (a) above comprises the steps of:

(f) providing a double skinned membrane with the correct pore size distribution; and In another preferred embodiment, step (d) above comprises the steps of:

(h) positioning a mask on the opposing membrane surface and sputtering an amorphous conductive surface to the membrane surface to form independent electrodes;

(i) said second exposed conductive surface area comprising (i) a counter electrode comprising a second electrode having a second electrode area, a second lead and a second contact pad, and optionally (ii) a reference electrode comprising a third electrode having a third electrode area, a third lead and a third contact pad.

In further preferred embodiment, step (d) above further comprises the steps of:

(o) positioning a second mask on the opposing surface so that the opposing electrode area is masked and the third reference electrode area is exposed;

(p) applying a reference material the third electrode area;

(q) removing the mask.

Preferably, the process employed to prepare the test devices of this invention is a continuous process. The ability to use continuous processing to fabricate the test devices, such as a continuous process utilizing continuous roll coating, continuous roll sputtering, continuous sputtering systems utilizing contact masks, results in high volume manufacturing capability and substantial cost reductions over the step and repeat printing processes.

DETAILED DESCRIPTION OF THE INVENTION

Figure 1:
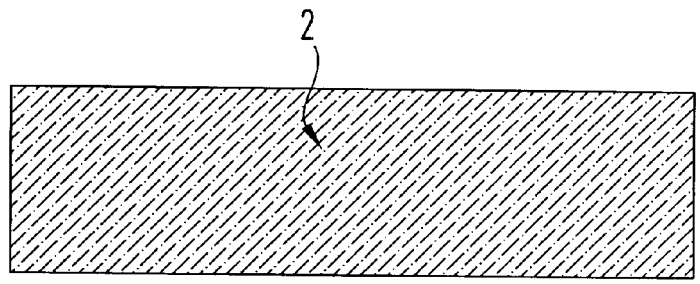
FIG. 1 illustrates a plan view of the membrane showing the top side and amorphous semiconductor coating.

The present invention utilizes amorphous semiconductor materials and double skin membranes to provide an electrochemical test device suitable for determining the presence or concentration of analytes in aqueous fluid samples. By using amorphous semiconductors and the double skinned membranes, uniform electrochemical test devices having well-defined reproducible electrode areas can be manufactured economically. These areas have very uniform surface morphology which reduces the variability of the electrochemical test. The surface morphology is directly related to the surface area of the electrodes. The amount and concentration of applied reagents are also critical to producing an accurate test. If the surface area is not consistent from device to device then the individual devices manufactured have to be individually calibrated to insure accurate readings in a meter. The test devices of the present invention permit highly accurate electrochemical analyte measurements to be performed on very small aqueous fluid samples due to the accurate reproduction of the test devices using controlled deposition methods such as sputtering, vapor phase deposition, glow discharge methods or evaporation and the very uniform surface of the double skin membranes to form the geometries. These devices can also be readily manufactured due to the lower cost and flexible nature of the amorphous semiconductor materials which allow the use of volume production in continuous processing manufacturing methods.

Thin film technologies are preferred for forming the amorphous semiconductor material layer or coating, such as sputtering, vapor phase deposition, glow discharge methods or evaporation. Such processes are capable of producing coatings up to a thickness of a few microns and of applying the coatings uniformly over the entire surface. If desired, thick film technologies are capable of producing much thicker layers in the range of less than 0.005 inches. While both methods can produce uniform surfaces, thin film surface morphology is dependent on the surface roughness of the underlying substrate, whereas the thick film technologies are capable of changing the final surface morphology of the device due to their thicker structure.

The electrochemical test device of this invention employs at least two types of electrodes. The first type of electrode is referred to as the "working or indicating electrode" and the second type is referred to as the "counter or opposing electrode". These electrodes permit changes in potential between the electrodes to be accurately measured when the analyte is applied across the electrodes, and the reagent reactive with the analyte is bound to the membrane matrix between the electrodes formed on the skin. Optionally, the test device may also contain a reference electrode. The reference electrode allows accurate measurements of potential to be made with respect to a fixed reference point. Any suitable reference electrode may be used, include silver/silver chloride, mercury/mercury chloride and platinum/hydrogen reference electrodes. Preferably, the reference electrode is a silver/silver chloride reference electrode and the working electrode has a potential ranging from about +1 to −1 volts versus the reference electrode. Reference electrodes suitable for use in this invention are further described in R. S. C. Cobbold, *Transducers for Biomedical Measurements: Principles and Applications*, pp. 343–349, John Wiley & Sons (New York).

The electrodes in the test device of this invention are manufactured using a double skinned membrane. Any suitable dielectric material may be used as the material for the membrane matrix as long as a tight pore skin can be formed on both sides of the membrane. For example, polysulphone, polyethersulphone, or nylon and is casted with a tight pore skin on each side and a relatively isotropic matrix between each ski surface. The skin pore size is relatively tight approximately 0.1 to 0.5 microns in size and the isotropic matrix being 0.5 microns or greater in pore size. Such polymeric materials are well known in the art and are commercially available. The membranes employed in preferred embodiments of this invention is Supor 200 available from Pall Gelman Sciences The electrodes are then prepared on the membrane using semiconductor manufacturing techniques. Typically, a conductive layer is first deposited on or applied to the membrane. The conductive layer comprises an amorphous semiconductor material, such as amorphous silicon oxide, amorphous carbon, gold or silver and the like. Amorphous metals can be formed by permitting a small amount of helium gas to escape in the sputtering chamber during sputtering. Such materials are well known in the art. For example, formation of suitable amorphous semiconductor films are described in U.S. Pat. No. 4,226,898, to Ovshinsky, the disclosure of which is incorporated herein by reference in its entirety.

Preferably, the amorphous semiconductor material employed in this invention is doped with lithium, potassium, or a similar conducting ion to increased conductivity. U.S. Pat. Nos. 3,983,076, and 4,178,415, to Ovshinsky, describe suitable methods for adding various compounds to amorphous semiconductor material to increase its conductivity. The disclosures of these patents are incorporated herein by reference in their entirety.

The amorphous semiconductor material is preferably deposited on the non-conducting membrane skin to form a conductive layer having a thickness of less than about 0.005 inches, more preferably a thickness ranging from about 1 to about 5 microns. The amorphous semiconductor material may be applied to the membrane using any art recognized procedure to form a conductive layer, such as sputtering, vapor phase deposition, glow discharge deposition, evaporation and the like. Alternatively, other deposition techniques such as electroplating, thick film laminating, roll transfer and the like may be employed. Thinner films are best achieved by sputtering, evaporation, vapor phase deposition, glow discharge methods or other thin film deposition method whereas thicker films are best formed using thick film deposition techniques such as electroplating, thick film laminating, roll transfer and the like. Charles A. Harper, *Handbook of Materials and Processes for Electronics*, 1984, (Library of Congress card number 76-95803) discusses various methods of forming thin films in Chapter 11, describes various thick film process in Chapter.

Preferably, the amorphous semiconductor material is deposited using vapor phase deposition or sputtering techniques. In a particularly preferred embodiment, the amorphous semiconductor material is formed by co-deposition of the amorphous semiconductor material and the doping material such as by co-vacuum deposition or co-sputtering. Co-sputtering can be accomplished in a conventional DC or RF. sputtering system, such as available from ULVAC Vacuum Systems. In this process, a cathode or target is bonded to a standard aluminum backing plate and is made of the semiconductor material to be deposited. Also, pieces of the doping material are secured to the cathode or target. Substrates upon which the amorphous semiconductor material and the doping material are to be deposited are carried by a holder located from the target by a distance of about 3.5 cm for a 3⅓" diameter cathode or passed continuously by the target.

The sputtering machine is first evacuated to a vacuum pressure somewhat less than about $6\times10^{-6}$ torr to provide a background vacuum pressure. Argon is bled into the machine to provide an operating pressure of about $5\times10^{-3}$ torr as determined by a reading on a Pirani vacuum gauge, giving an actual vacuum pressure of about $7\times10^{-3}$ torr in the machine. The surface of the cathode or target and pieces of doping material are first cleaned by sputtering against the shutter of the machine adjacent to substrates for about 30 minutes. Thereafter, the shutter is opened and the semiconductor material of the target and the pieces of doping material on the target are co-sputtered onto the non-conductive coating or substrate. The cathode or target and the holder for the substrates are both water cooled so that their temperature is low during the sputtering operation, as for example, approximately 50° C. The RF. power of the machine may have a frequency of about 13.56 MegaHertz, and about 1000 Volts of forward power, about 50–70 Watts being utilized for 3.5" diameter cathode or target.

The deposition rates depend upon the materials being sputtered, and the time of deposition is varied to obtain desired thicknesses of the deposit. The thicknesses of the simultaneously deposited amorphous semiconductor film having the doping material therein may vary from a few hundred anastroms to about 5 microns ($5\,\mu$), depending upon the uses to which the amorphous semiconductor film is to be put. The amorphous semiconductor material is deposited on the membrane.

The amount of doping material homogeneously incorporated in the amorphous semiconductor material is generally determined by the area of the pieces of the doping material applied to the semiconductor material of the cathode or target. Desired percentage of modifier material added to the amorphous semiconductor material may accordingly be conveniently controlled. By utilizing co-sputtering as generally here described, the doping material is substantially homogeneously incorporated in the semiconductor material to provide the beneficial features of this invention.

Preferably, the amorphous semiconductor material is applied continuously to the membrane using art recognized continuous processes. Such continuous processes are described, for example, in U.S. Pat. No. 3,983,076, to Rockstad, and in U.S. Pat. Nos. 3,271,591 and 4,178,415, to Ovshinsky, the disclosures of which are incorporated herein by reference in their entirety. The ability to use continuous processing to fabricate the test devices of this invention, such as a continuous process utilizing continuous roll coating, continuous roll sputtering, results in high volume manufacturing capability and substantial cost reductions over the step and repeat processes currently used. Suitable machines for such continuous processes are made by Ulvac Vacuum Systems of Japan.

Optionally, if a reference electrode is used, the third electrode, if present, is constructed by using a contact mask which isolates the two electrodes formed on the bottom skin. The contact mask permits only application of sputtered material in the open areas and does not permit the coating on the covered areas. The reference electrode is then converted into a reference electrode by applying a suitable reference material. Suitable reference materials include silver/silver chloride, a mercury/mercury chloride and platinum/hydrogen materials. Such materials can be applied to the third electrode area of the reference electrode by any thin film deposition method described above.

A particularly preferred reference material is silver/silver chloride. In order to obtain consistent results from device to device, the silver/silver chloride layer must be applied such that the silver/silver chloride layer covers essentially the same surface area in each device manufactured. Preferably, this is accomplished using a contact mask as described above to expose a precise area of the electrode after developing. A thin layer of silver is then deposited on the exposed area, preferably by sputtering or other consistent film application method. The silver layer is preferably less than about 0.001 inches in thickness, more preferably about 1 micron to about 5 microns in thickness. Alternatively, a silver layer can be applied to the electrode area of the reference electrode using pad printing, inkjet methods, transfer roll printing or similar techniques. The silver layer is then contacted with $FeCl_3$ solution to convert the silver surface to silver chloride thereby forming a silver/silver chloride layer The electrochemical test device is then completed by applying an appropriate reagent to the membrane. The reagent is imbibed into the membrane matrix under the sample application area. Suitable reagents for determining the presence or concentration of various analytes are well known in the art and are described in further detail herein below.

Preferred Process for Preparing the Electrodes

As described above, the electrodes for the electrochemical test device of this invention are prepared using amorphous semiconductor materials and double sided skinned membrane. Preferably, such electrodes are formed in a continuous manner. A preferred process for the preparation of electrodes suitable for use in this invention is illustrated in FIGS. 1–9.

Figure 2:
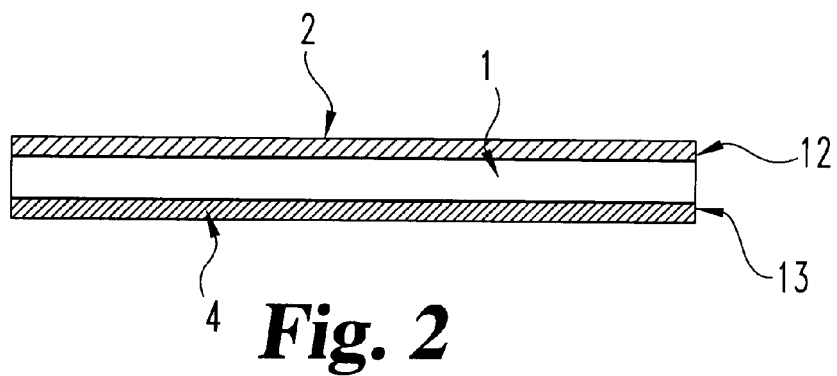
FIG. 2 illustrates a side view of the membrane showing the skin and amorphous semiconductor coatings.
Figure 3:
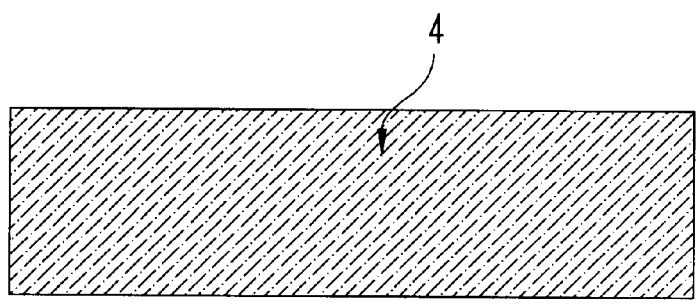
FIG. 3 illustrates a plan view of the membrane showing the bottom side and amorphous semiconductor coating.

As illustrated in FIGS. 1, 2 and 3, the membrane 1 which has skins 12 and 13 is coated with amorphous semiconductor material creating surfaces 2 and 4 which are the electrodes have a thickness of less than about 0.005 inches and preferable in the range of 1 to 5 microns.

Figure 4:
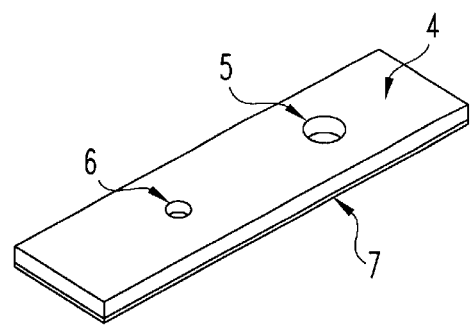
FIG. 4 illustrates an isometric view of the non conductive top layer.

FIG. 4 shows an isometric view of the top non conductive layer 4 which has been coated with adhesive 7. Non conductive layer 4 has holes 5 and 6 punched in the layer. Hole 5 is the sample application hole and permits the application of the indicating reagent during manufacture. Hole 6 is permits the measuring device to contact the conductive surface of the membrane.

Figure 5:
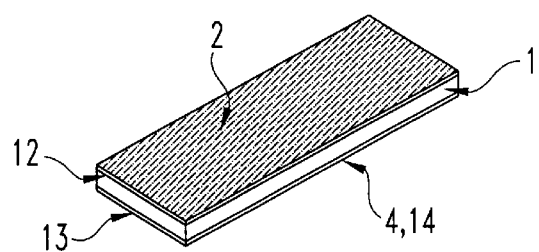
FIG. 5 illustrates an isometric view of the double skin membrane with conductive layers.

FIG. 5 shows an isometric view of the membrane with conductive layers 2 and 4 and reference coating 14 (not shown) applied to the opposite side of the membrane.

Figure 6:
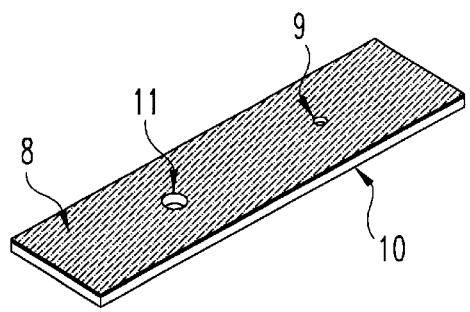
FIG. 6 illustrates an isometric view of the non conductive bottom layer.

FIG. 6 shows an isometric view of the bottom non conductive layer 10 which has been coated with adhesive 8. Non conductive layer 10 has holes 9 and 11 punched in the layer. Hole 9 is the sample vent hole and permits the venting of the air in the membrane during application of the indicating reagent when the strip is manufactured. Hole 11 is permits the measuring device to contact the conductive surface of the membrane.

Figure 7:
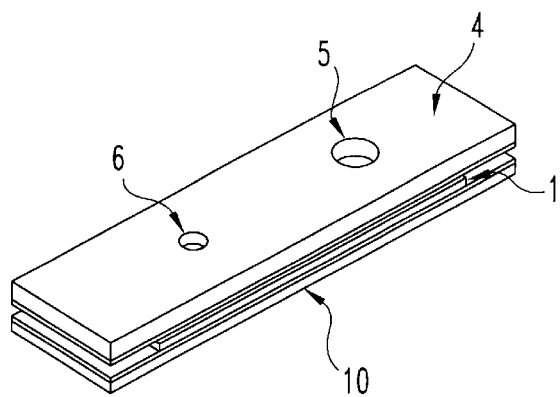
FIG. 7 illustrates an isometric view of the assembled device.

FIG. 7 is an isometric view of the finished device showing the membrane 1 sandwiched between the top and bottom non conductive layers 4 & 10 with top vent hole 5 and top contact hole 6.

Figure 8:
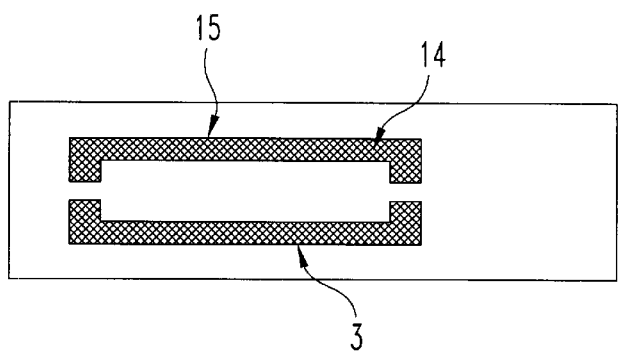
FIG. 8 illustrates finished reference and opposing electrode.

As shown in cross section FIG. 8 is a bottom view of a membrane showing opposing electrode 3 and reference electrode 15 with reference coating 14. The pattern is formed by sputtering on the skin and using a contact mask to pattern the electrodes.

Figure 9:
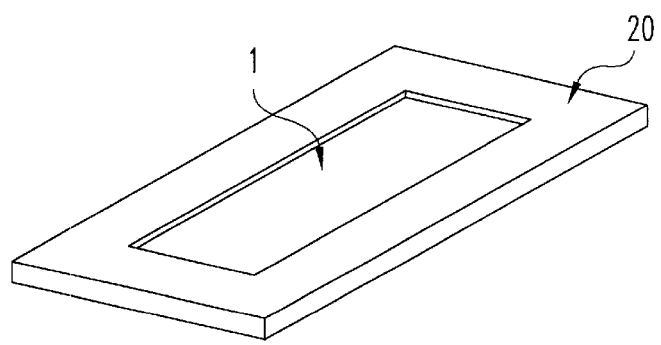
FIG. 9 illustrates an isometric view of membrane position in a sputter frame.

As illustrated in FIG. 9, the membrane 1 can be loaded into a frame 20 to permit discrete manufacturing.

Reagents

Various types of analytical or electrochemical sensor reagents may be applied to the electrodes. To create a functional electrochemical test device, a reagent chemistry must be selected based on the analyte to be tested and the desired detection limits. Preferably, the reagent is deposited on the membrane such that a uniform amount is applied from sensor to sensor. The reagent may be applied using any conventional procedure, such as nozzle coating through the hole 5 in layer 4 using IVEK pumps or any other drop on demand system capable of delivering consistent and uniform volume of reagent.

The reagent is applied through the working electrode, but may in some cases also be applied through the other electrodes. After the reagent has been imbibed into the membrane, it is typically dried. Subsequently, when the test device is used, the test sample of aqueous fluid, such as blood, rehydrates the reagent and a potential is applied to the electrodes from which a current measurement may be taken by a meter. The membrane matrix acts as reagent carrier and electrode spacer. This permits the device to have a reduced manufacturing cost due to the excellent uniformity of the membrane thickness and isotropic nature of the inner matrix of the membrane.

An example reagent formulation suitable for use in the present invention is described below. This reagent may be used to determine the presence or concentration of glucose in an aqueous fluid sample. Preferably, this reagent formulation is used with an electrochemical sensor having an opposing electrode 3, working electrode 2 and reference electrode 15.

Reagent Formulation

| Material | Amount/ Concentration |
| --- | --- |
| 2-(N-morpholino)ethanesulfonic acid (MES buffer) | 100 millimolar (mM) |
| Triton X-100 | 0.08% wt/wt |
| Polyvinyl alcohol (PVA) mol. wt. 10K 88% hydrolyzed | 1.00% wt/wt |
| Imidazole osmium mediator, reduced, as defined in U.S. Pat. No. 5,437,999 | 6.2 mM |
| Glucose Oxidase | 6000 units/mL |

The above reagent formulation may be prepared using the following procedures:
(a) 1.952 grams of MES buffer is added to 85 mL of nanograde water. The mixture is stirred until the components dissolve. The pH of the solution is adjusted to 5.5 with NaOH. The volume of the solution is then brought to 100 mL of final buffer solution.
(b) 0.08 grams of Triton X-100 and 1 gram of PVA is added to a beaker capable of holding all the components (e.g., a 200 mL beaker). The buffer solution is added to bring the total solution weight to 100 grams. The mixture is heated to boiling and stirred to dissolve the PVA.
(c) 4.0 mg of the reduced osmium mediator is added to 1 mL of the solution from step (b) above. The mixture is stirred to dissolve the mediator.
(d) The mixture is left to cool to room temperature.
(e) 6000 units of glucose oxidase are added and the mixture is mixed until the enzyme is dissolved.

The above reagent formulation may be used to determine the presence or concentration of glucose in an aqueous fluid sample. As will be apparent to those skilled in the art, other reagent formulations may be employed to assay different analytes. Such reagent formulations are well known in the art. Typically, such reagent formulations are designed to react specifically with the desired analyte to form a measurable electrochemical signal.

Without being limited to theory, it is believed that in the example reagent formulation described above, glucose is anaerobically oxidized or reduced with the involvement of the enzyme and the redox mediator. Such a system is sometimes referred to as an amperometric biosensor. Amperometry refers to a current measurement at constant applied voltage on the working electrode. In such a system, the current flowing is limited by mass transport. Therefore, the current is proportional to the bulk glucose concentration. The analyte, enzyme and mediator participate in a reaction where the mediator is either reduced (receives at least one electron) or oxidized (donates at least one electron). The glucose reaction ends when glucose oxidase is oxidized and the mediator is reduced. The mediator is then oxidized at the surface of the working electrode by the applied potential difference. Changes in the system amperage result from changes in the ratio of oxidized/reduced form of the redox mediator. The amperage change directly correlate to the detection or measurement of glucose in the test sample.

Various enzymes may be used in the reagent formulations employed in this invention. The particular enzyme employed will vary depending on the analyte to be detected or measured. Preferred enzymes include glucose oxidase, glucose dehydrogenase, cholesterol esterase and alcohol oxidase. The amount of enzyme employed will generally range from about 0.5 to about 3.0 million units of enzyme per liter of reagent formulation.

The reagent formulation will also typically contain a redox mediator. The redox mediator will generally be chosen to be compatible with the enzyme employed and combinations of redox mediators and enzymes are well known in the art. Suitable redox mediators include, by way of example, potassium ferricyanide and ferrocene derivatives, such as 1,1¢-dimethyl ferrocene. The amount of redox mediator employed in the reagent formulation will typically range from about 0.15M to about 0.7M. Additional mediators suitable for use in this invention include methylene blue, p-benzoquinone, thionine, 2,6-dichloroindophenol, gallocyanine, indophenol, polyviologen, osmium bis(2,2¢-bipyridine) dihydrochloride, and riboflavin-5¢-phosphate ester. Optionally, these mediators can be chemically bound or entrapped in a matrix, such as a polymer, using procedures well known in the art.

Examples of enzyme/mediator combinations suitable for use in this invention include, but are not limited to, the following:

| Analyte | Enzyme | Mediator |
| --- | --- | --- |
| glucose | glucose dehydrogenase | ferricyanide |
| glucose | glucose oxidase | tetracyanoquinodimethane |
| cholesterol | cholesterol esterase | ferricyanide |
| alcohol | alcohol oxidase | phenylenediamine |

A preferred reagent chemistry uses potassium ferricyanide as a mediator.

In addition to an enzyme and a redox mediator, the reagent layer on the electrode preferably further comprises a buffer, a stabilizer, a dispersant, a thickener or a surfactant. These materials are typically employed in amounts which optimize the reaction of the reagents with the analyte. The concentration ranges for these components referred to below are for the reagent formulation before it has dried on the electrode surface.

A buffer is preferably employed in the reagent formulation to provide a satisfactory pH for enzyme function. The buffer used must have a higher oxidation potential than the reduced form of the redox mediator. A preferred buffer for use in this invention is a phosphate buffer having a concentration ranging from about 0.1M to about 0.5M. Other suitable buffers include BES, BICINE, CAPS, EPPS, HEPES, MES, MOPS, PIPES, TAPS, TES and TRICINE buffers (collectively known as 'GOOD' buffers), citrate, TRIS buffer, and the like. The 'GOOD' and TRIS buffers are commercially available from Sigma-Aldrich, Inc. (St. Louis, Mo., U.S.A.).

A stabilizer may also be employed in the reagent formulation to stabilize the enzyme. When the enzyme used is glucose oxidase, a preferred stabilizer is potassium glutamate at a concentration ranging from about 0.01 to 4.0% weight. Other suitable stabilizers include succinate, aspartate, blue dextran and the like.

Additionally, dispersants may be used in the reagent formulation to enhance the dispersion of the redox mediator and to inhibit its recrystallisation. Suitable dispersants include microcrystalline cellulose, dextran, chitin and the like. Typically, the dispersant is used in the reagent formulation in an amount ranging from about 1.0 to about 4.5% weight. Preferred dispersants include, but are not limited to, AVICEL RC-591 (a microcrystalline cellulose available from FMC Corp.) and NATROSOL-250 M (a microcrystalline hydroxyethylcellulose available from Aqualon).

A thickener may also be employed in the reagent formulation to hold the reagent to the electrode surface. Suitable thickeners include water soluble polymers, such as polyvinylpyrrolidone.

Additionally, a surfactant may be added to the reagent formulation to facilitate rapid and total wetting of the electrode surface. Preferably, the reagent formulation contains a nonionic surfactant in an amount ranging from about 0.01 to 0.3% by weight. A preferred surfactant is TRITON X-100, available from Sigma-Aldrich, Inc.

Use of the Electrochemical Test Device

To illustrate the use of an electrochemical test device of this invention, the following glucose assay is described. It will be understood, however, that by selecting the proper reagent, other analytes may be determined using these procedures.

The electrodes of the electrochemical test device are prepared as described above and the membrane is coated with 1.0 μL of the above-described reagent formulation and dried.

The electrochemical test device is then inserted in a meter before the test sequence is initiated. Any suitable meter device which has contacts that interface with the test device contacts may be employed. Such metering devices are well known in the art. The meter will generally contain a measuring circuit and be adapted to apply an algorithm to the current measurement whereby the analyte level is provided and visually displayed. Examples of suitable power sources and meters may be found, for example, in U.S. Pat. Nos. 4,963,814, 4,999,632, and 4,999,582 to Parks et al., U.S. Pat. No. 5,243,516 to White et al., and European Patent Application No. 89116797.5, to Hill et al. The disclosures of these patents are incorporated by herein by reference in their entirety.

A small sample of blood or other aqueous fluid is then applied to the test device. The current is measured about 10 to about 30 seconds after applying the sample. The current is read by the meter between the working and counter electrode and, optionally, is compared to the reference electrode, if it is present. The meter then applies the algorithm to the current measurement and converts the measurement to an analyte concentration. This analyte level is visually displayed on the meter.

From the foregoing description, various modifications and changes in the electrochemical test devices, processes and methods of this invention will occur to those skilled in the art. All such modifications coming within the scope of the appended claims are intended to be included therein.

Additional materials and methods useful in this invention are disclosed in copending applications Ser. No. 60/019,864 filed Jun. 17, 1996 and Ser. No. 08/876,812 filed Jun. 17, 1997, the disclosures of which are incorporated herein by reference in their entirety.

What is claimed is:

1. An electromechanical test device for determining the presence or concentration of an analyte in an aqueous fluid sample, said electromechanical test device comprising:

a. a non-conductive membrane having a first skin and a second skin and a matrix therebetween;

b. a working electrode comprising an amorphous semiconductor material affixed to the non-conductive membrane first skin, said working electrode having a first electrode area, a first lead and a first contact pad;

c. an opposing electrode comprising an amorphous semiconductor material affixed to the non-conductive membrane second skin, said opposing electrode having a second electrode area, a second lead, and a second contact pad; and d. a reagent capable of reacting with the analyte to produce a measurable change in potential which can be correlated to the concentration of the analyte in the fluid sample, said reagent imbibed in the membrane matrix between the working electrode and opposing electrode;

wherein said reagent comprises an enzyme and a redox mediator, wherein said enzyme is a member selected from the group consisting of glucose dehydrogenase, glucose oxidase, cholesterol esterase, and alcohol oxidase, and wherein said redox mediator is a member selected from the group consisting of ferricyanide, tetracyanoquinodimethane, and phenylenediamine.

2. The electrochemical test device of claim 1 wherein said ferricyanide is potassium ferricyanide.

3. An electromechanical test device for determining the presence or concentration of an analyte in an aqueous fluid sample, said electromechanical test device comprising:

a. a working electrode comprising an amorphous semiconductor material;

b. an opposing electrode comprising an amorphous semiconductor material; and c. a reagent capable of reacting with the analyte to produce a measurable change in potential which can be correlated to the concentration of the analyte in the fluid sample, said reagent located between the working electrode and opposing electrode;

wherein said reagent comprises an enzyme and a redox mediator; wherein said enzyme is a member selected from the group consisting of glucose dehydrogenase, glucose oxidase, cholesterol esterase, and alcohol oxidase; and wherein said redox mediator is a member selected from the group consisting of ferricyanide, tetracyanoquinodimethane, and phenylenediamine.

4. The electrochemical test device of claim 3 wherein said ferricyanide is potassium ferricyanide.

* * * * *